Figure 1:
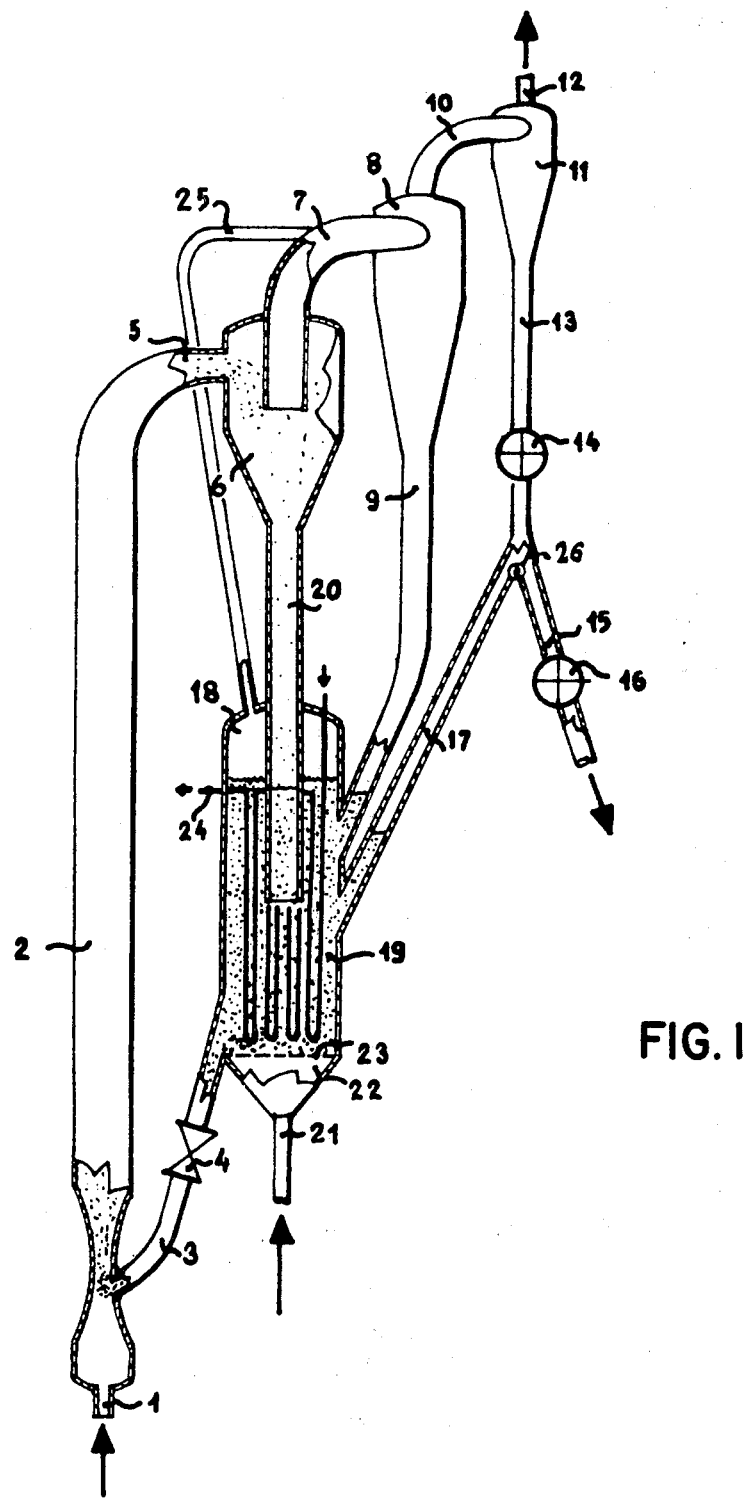

United States Patent [19]

Becuwe

[11] 3,952,022

[45] Apr. 20, 1976

[54] METHOD OF CONDENSING PHTHALIC ANHYDRIDE

[75] Inventor: Jacques Becuwe, Fontenay-sous-Bois, France

[73] Assignee: Rhone-Progil, Courbevoie, France

[22] Filed: Jan. 14, 1974

[21] Appl. No.: 433,259

[30] Foreign Application Priority Data

Jan. 16, 1973 France .............................. 73.01371

[52] U.S. Cl. ........................ 260/346.7; 23/252 R; 23/259
[51] Int. Cl.² ...................................... C07D 307/82
[58] Field of Search ................................. 260/346.7

[56] References Cited
UNITED STATES PATENTS

| | | | |
|---|---|---|---|
| 2,583,013 | 1/1952 | Patterson | 260/346.7 |
| 2,702,091 | 2/1955 | Smith | 260/346.7 |

*Primary Examiner*—Harry I. Moatz
*Attorney, Agent, or Firm*—McDougall, Hersh & Scott

[57] ABSTRACT

A method of condensing and recovering phthalic anhydride in dilute concentration in gases discharged from reactors. The method comprises condensing the anhydride on a solid granular carrier moving in a pneumatic conveyor, separating the condensate from its carrier and cooling the said carried in a fluidized bed for recycling it. The method is also application to the condensation of other sublimable substances.

5 Claims, 2 Drawing Figures

METHOD OF CONDENSING PHTHALIC ANHYDRIDE

The invention relates to a method of continuously condensing phthalic anhydride diluted in air, on a solid thermal carrier (caloporteur).

It is known that phthalic anhydride can be condensed, possibly continuously, at the outlet of the reactors in which it is obtained, on solid particles of the same compound or on an inert granular carrier. Condensation takes place in a fluidized bed cooled by a heat exchanger immersed in the bed. The condensate is generally recovered by melting in a special vessel. Alternatively, when a granular carrier is present, it may advantageously be recovered by projecting pellets covered with the condensate against a stationary wall, as described in applicants' French Patent Application No. 71.32,531 of Sept. 9, 1971, entitled "A continuous Method of Recovering Sublimable Substances by Condensation in the solid State," corresponding to United States application Ser. No. 284,348, filed Aug. 28, 1972.

With the latter method, there is a marked simplification in the condensing apparatus and an improvement in the thermal balance as compared with discontinuous methods using condensers with stationary surfaces. For economic reasons, however, the condensation region used in this method is subject to certain limitations (shallow bed and large diameter in particular). Furthermore, the fact that condensation and heat exchange (elimination of heat) take place simultaneously within the same chamber, makes the apparatus rather inflexible, while the chamber is subject to fouling, which is difficult to avoid.

The method of the invention avoids these drawbacks by separating in space the condensation phase from the heat elimination phase.

The invention concerns a method of condensing and recovering phthalic anhydride diluted in the gases discharged from reactors, comprising condensing the anhydride on a solid granular carrier moving in a pneumatic conveyor, separating the condensate from the carrier and recovering a quantity of condensate substantially equal to the quantity deposited, cooling the carrier in a fluidized bed at a temperature below that at which the anhydride solidifies, and then returning said carrier for recirculation in the condensation zone.

It is understood, of course, that the different phases of condensation, separation and cooling take place simultaneously and continuously in different parts of the apparatus employed. It is possible, however, without going beyond the scope of the invention, if, for example, the separation and recovery of the condensate is effected discontinuously in a closed container, by melting the condensate deposited on an inert carrier, with the quantity of the carrier present in the cycle remaining sufficient to permit normal operation of the other phases.

The condensation phase is carried out in a reaction zone which is conventionally in the form of a vertical cylinder, at the base of which is introduced (a) the effluent gases resulting from the oxidation of hydrocarbons, such as o-xylene or naphthalene, in one or more reactors, and (b) the granular carrier which is caused to move upward by said gases. The height of this reaction zone is usually from 1 to 10 meters.

The gaseous effluents may be diluted, e.g. by supplying fresh air such that the partial pressure of the condensable substance enables the product to be directly converted to the solid phase, by lowering the temperature and/or by cooling the gases to a temperature of at least 5°C below the solidification temperature of the anhydride.

The granular carrier may be of various types; it may consist of phthalic anhydride grains or some inert material. In the latter case it is preferable that the material be hard and non-friable, have a specific density above 1 and possess some elasticity, and it should also be able to retain its physical properties under the temperature conditions prevailing in the apparatus and in the presence of the substances contained therein, and its shape should be approximately spherical. Pellets of glass, silica, ceramics, metals such as aluminum or stainless steel, heat-stable plastics such as fluorinated polymers of ethylene or grains of sand would comply with these requirements. The proportion of carrier solids, at the outlet from the condensation tube, should generally be from 0.5 to 40 kilograms per kilogram of gas, and its average diameter should be from 50 microns to 3 millimeters. This concentration of solids in the gases is calculated as a function of the temperature difference between the effluent gases and the carrier when they arrive in the condensation region, and of the quantity of heat which has to be absorbed. The grain size is selected so as to give an adequate exchange surface, to permit easy circulation in the various parts of the apparatus and to allow for easy and complete separation from the gases. Apart from its ability to condense virtually all the phthalic anhydride emerging from the reactors, the carrier thus should be set in motion in a pneumatic conveyor. For such movement to take place, the speed of the effluent gases (depending particularly on the cross-section of the condensation region) must be higher than the final speed of the free fall of the grains of carrier. This speed is generally from 2 to 50 m/sec. for the grain size in question.

When one knows the weight of carrier used for a certain weight of gas, the temperature of the gases and their composition, it is a simple matter to calculate the maximum temperature at which the carrier should be placed in the condensation region to insure that the phthalic anhydride will condense. The minimum temperature is governed by the condensation temperature of certain vapors present in the gases and particularly the dew point of water. The flexibility of the method is due particularly to the fact that, even if several parameters are imposed for various reasons, the user still has great latitude in his choice of many others, while still observing the requirements emphasized above.

The phase in which the condensate is separated will hereinafter be described in greater detail in the description of the apparatus. The mode of separation varies considerably, depending on whether condensation takes place on solid anhydride or on an inert carrier. In the former case, it is preferable for the larger grains, separated by the known means, to be recycled while the finer grains are withdrawn. The wear which takes place in the various sections of the apparatus keeps these grains at a substantially constant size. In cases where a different type of carrier is present, the condensate deposited around the grains of inert material is detached from its carrier by projection onto a stationary surface. The condensate which surrounded each granule is fragmented by the shock and directed towards an outlet where it is collected, while the carrier is recycled; the separation of the granules from the fragments of anhydride, which is made possible by the difference in specific gravity and grain size, is carried out by known apparatus.

The elimination of heat from the carrier takes place in a fluidized bed with a heat exchanger submerged therein. Fluidization is brought about by passing fresh air below the bed, or alternatively gas which has been recycled following the recovery of the solid which it carried. The conditions which have to be observed in fluidization are also well known and depend on the nature and size of the grains of solids forming the bed. The minimum volume of the bed depends on the area of heat exchanger submerged therein. The speed of the fluidizing gas is generally from 0.05 to 2.5 meters/second. The temperature to which the carrier has to be cooled in the fluidization bed is that which should obtain at the inlet to the condensation region; the carrier does not in fact generally undergo any marked change in temperature between the two chambers.

This displacement of the carrier, which closes its circuit, may be brought about by various means and particularly by gravity. A conventional arrangement enables its output to be controlled so as to maintain a substantially constant quantity of carrier in the condensation region.

The method of the invention will now be described with reference to diagrams of the apparatus in which it can be employed. The description is given to illustrate the invention; it does not exclude other embodiments and should not be considered as restricting its scope.

Figure 2:
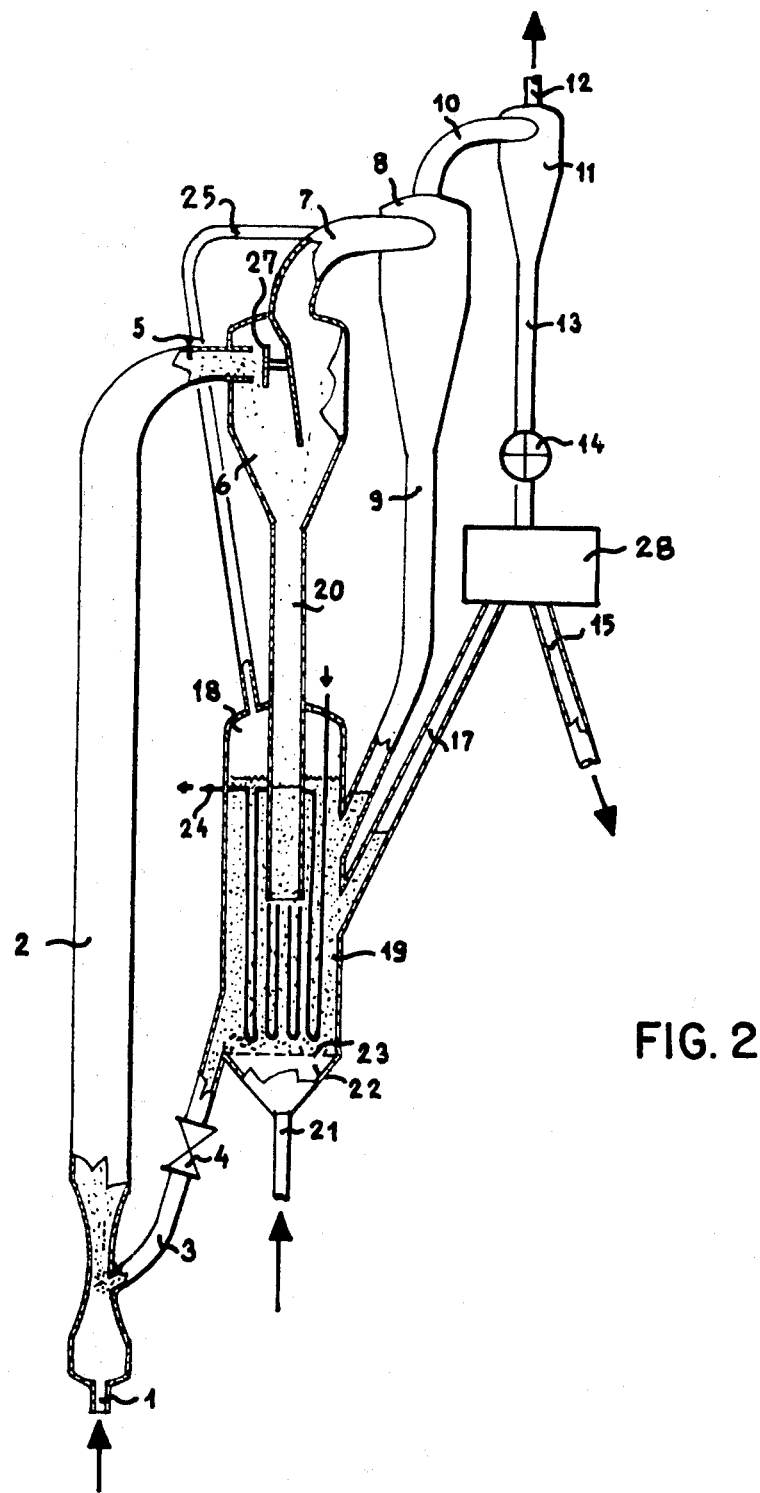

In the drawings:

FIG. 1 is a diagram of apparatus designed for the embodiment in which the condensate carrier is phthalic anhydride; and FIG. 2 is a diagram of apparatus for applying the invention in cases where the carrier is an inert material.

Referring now to FIG. 1, 1 is the tube through which the effluent gases from the reactor or reactors arrive, possibly diluted with fresh air and/or cooled by passage through a heat exchanger (not shown). The tube 1 discharges into the lower part of a vertical condensation chamber 2, which is curved, near the inlet of another tube 3 supplying the granular carrier, the output of which is controlled by the valve 4.

The condensation chamber opens at its upper end 5 into an expansion chamber 6 for the crude removal of dust from the gases. The gas stream and residual solids issue through a pipe 7 to a cyclone 8, which is provided at the bottom with a pipe 9 for the separated solids and at the top with a pipe 10 through which the gases are directed to a second cyclone 11. The gases issue therefrom through an outlet 12, possibly to a cleansing device (not shown). The solids separated by the cyclone pass down a pipe 13, provided with a device 14, such as a pneumatic valve or a rotating distributor, which prevents the gases from circulating upwardly but allows some of the solids to flow away to a vessel (not shown) through a tube 15. The output is controlled by a valve 16. The excess is directed through a different tube 17 to a chamber 18 containing a fluidized bed 19 of grains of anhydride. The substance separated in chamber 6 and cyclone 8 flows through tubes 20 and 9 respectively, to the fluidized bed. Fluidization is brought about by passing air or gas recycled from aperture 12 through the aperture 21, which is provided at the bottom of a frustoconical portion 22 of the chamber 18. A grid 23, arranged at the level of the large end of the truncated cone, supports the granular bed when it is at rest and provides for the distribution of the fluidizing gases during operation. A heat exchanger 24, submerged in the bed, cools the grains forming the bed. The conduit 3, which completes the circuit of the condensation carrier, communicates the condensation region 2 with the chamber 18 slightly above the grid 23. A tube 25 enables the gases passed into the fluidized bed to pass through the chamber 6 and the cyclones 8 and 11 for issuance from the outlet 12. A valve 26, located at the junction of the tubes 13, 15 and 17, controls the output ratio of the tubes 15 and 17.

The apparatus shown diagrammatically in FIG. 2 is very similar to that in FIG. 1. In pipe 2, which acts as the condensation region, the phthalic anhydride is deposited on grains or pellets of inert material. The greater part of the condensate is detached from its carrier within the expansion chamber 6. The upper portion 5 of the pipe 2 is in fact modified to form a neck which extends into the chamber 6 with an exit opening parallel with the axis of the pipe 2 and a suspended partitioning plate 27. The distance between the opening and the plate is some few centimeters (2 to 40 cm). The stream of gas projects the granular carrier covered by a layer of the deposit of condensed anhydride against that plate. The deposit breaks into several pieces like a wooden shell. It is not necessary for the speed at which the grains are projected to be very high; the above-mentioned neck increases it slightly, but the normal speed at which the solids are displaced within the pipe 2 is generally sufficient.

A portion of the pellets pass through the pipe 20. Another portion is carried through the cyclone 8 then into the cyclone 11, where more complete separation is effected. The solid fraction, recovered in cyclone 11, flows through tube 13, passes through the device 14, then undergoes screening in the apparatus 28, which is a separator, e.g. of the type generally known as an air classifier. The phthalic anhydride, which is isolated, is dispatched through conduit 15, while the grains of inert material are directed through pipe 17 to the chamber 18. The greater part of the pellets has already been directed towards this chamber through pipes 20 and 9.

The rest of the apparatus is similar to that in FIG. 1.

This method has important advantages over condensation processes in a cooled fluidized bed. The only cold elements in the condensation region are in fact the carrier grains. Condensation takes place solely on these grains, so there is no caking of the apparatus and no nucleation, i.e. no formation of fine dust of particles of about one micron or less. The only fine particles formed (of several microns) are due to the inevitable but in fact very slight wear, which moreover prevents any marked enlargement of the grains during recycling. The stirring action and heat exchange, which are excellent in the region where the gases from the reactors come into contact with the cold condensation carrier, insure a remarkable yield from the condensation; the time which the gases containing the anhydride have to spend in the contact region in order to achieve condensation is very short (less than 1 second). Moreover the chamber containing the fluidized bed is not subject to fouling, another factor which makes for optimum heat exchange.

The method has been described in its application to phthalic anhydride. It will be appreciated that other substances which can be condensed in the solid state, such as anhydrides of organic diacids, anthraquinone, salicylic acid, aluminum chloride, ammonium chloride, bromide and iodide and many metal halides can be condensed and recovered in this way.

Examples will now be given by way of illustration, but not by way of limitation, of the practice of the invention.

EXAMPLE 1

This example concerns the use of the method of the invention in which condensation takes place on grains of phthalic anhydride. The apparatus is in accordance with FIG. 1 with the condensation region in the form of a vertical pipe having an internal diameter of 10 cm and a height of 4 m. Gases, discharged from reactors for preparing phthalic anhydride through oxidation of o-xylene by air, are passed into this apparatus at a temperature of 160°C and at a rate of 306 kg/h. The weight ratio of anhydride to the total mixture of gases is 1/23. The gases are cooled on contact with granular phthalic anhydride entrained for pneumatic transportation in the gas stream. The amount of solids with which the gases are charged is 6.1 kg/kg. This charge is controlled by action on the valve 4. The grain size of the phthalic anhydride ranges from 10 to 200 microns. The mixture of gases and solids has a temperature of 55°C at the point of introduction into the expansion chamber.

The fluidized bed 3 m high, which is kept in suspension by a flow of 70 l/h of recycled gas at ambient temperature, is in a cylindrical chamber having a height of 4 m and an internal diameter of 35 cm. It is kept at 35°C by circulating water, which is introduced at 20°C, in 27 tubes 15 × 21 mm in area and 2.80 m in height, submerged in the bed.

When the installation is started up, 140 kg of phthalic anhydride with substantially the grain size indicated above is placed in the fluidization chamber. After a few cycles, a balance is quickly established, as far as this grain size is concerned.

13.3 kg/h of phthalic anhydride is extracted continuously and the remainder is recycled, thus keeping the weight of the circulating compound substantially constant.

EXAMPLE 2

This example concerns the application of the method of the invention in the embodiment where condensation takes place on an inert carrier. The apparatus is in accordance with FIG. 2. The vertical pipe (condensation region) is identical with that of Example 1. The outlet is parallel with a vertical partition 7 cm in diameter and is 15 cm away from the partition. Projection of the solids onto this wall causes the condensate to be detached from its carrier.

The effluent gases from the oxidation reactions have the same flow rate, the same composition and the same temperature as in the previous example when they arrive in the condensation pipe. The gases are cooled there and the phthalic anhydride is continuously condensed onto a carrier consisting of glass pellets of a grain size from 80 to 200 microns. The pellets become covered with phthalic anhydride fed in at the base of the pipe and are carried along in pneumatic transportation by the gases. The proportion of inert solid to total solid is 65 to 75% by weight. At the entrance to the pipe the amount of solids carried by the gases is 8.4 kg/kg; the temperature of the gases is 55°C.

The separation of the pellets from the anhydride, following the detachment of the condensate from its carrier, takes place in the expansion chamber and cyclones, then is continued in a separator of the "air classifier" or "elutriation" type. 18.5 kg/h of pellets and anhydride flow to this separator from the last cyclone, and 13.3 kg/h of phthalic anhydride is withdrawn therefrom. The pellets are returned into the chamber containing the heat exchanger and the fluidized bed. Apart from the separator just described and the device for projecting the pellets and breaking their shell of condensed substance, the apparatus is identical with that in the previous example.

5.2 kg/h of solid is recycled, out of which 5% by weight of phthalic anhydride is left.

I claim:

1. A method of condensing and recovering phthalic anhydride diluted in gases discharged from a reactor, in which the phthalic anhydride is produced by oxidation of o-xylene or naphthalene, comprising introducing the gaseous stream containing vapors of phthalic anhydride diluted in the gases discharged from the reactor for continuous flow through a confined passage the surfaces of which are free of cooling means which might cause condensation of phthalic anhydride thereon, introducing into the gaseous stream solid granular carrier at a temperature below the solidification temperature of the phthalic anhydride whereby phthalic anhydride condenses on the surfaces of the carrier during their conveyance by the gaseous stream through the confined passage; separating from the carrier and collecting a quantity of condensate substantially equal to the quantity condensed; cooling the carrier outside the pneumatic conveyor in a fluidized bed to a temperature below the solidification temperature of the anhydride; and then recycling the carrier back into circulation in the condensation region.

2. A method of condensing and recovering phthalic anhydride according to claim 1, characterized in that the condensation carrier is granular phthalic anhydride.

3. A method according to claim 1, characterized in that the condensation carrier is an inert granular material, and that the condensate is separated from its carrier by projecting the said carrier covered with condensate against a stationary wall.

4. A method according to claim 1, characterized in that the grains have average diameters within the range of 50 microns to 3 millimeters in the condensation region, and that the transporting gases circulate at a speed within the range of 2 to 50 meters/second.

5. A method according to claim 1, characterized in that the speed of the gases which produce fluidization in the cooling region is within the range of 0.05 to 2.5 meters/second.

* * * * *